United States Patent
Badoz

(10) Patent No.: US 7,431,588 B2
(45) Date of Patent: Oct. 7, 2008

(54) INSTRUMENT FOR REAMING ROOT CANALS AND SEQUENCE OF INSTRUMENTS COMPRISING AT LEAST SUCH AN INSTRUMENT

(75) Inventor: Jean-Marie Badoz, Doubs (FR)

(73) Assignee: Micro Mega International Manufactures, Besançon (FR)

( * ) Notice: Subject to any disclaimer, the term of this patent is extended or adjusted under 35 U.S.C. 154(b) by 0 days.

(21) Appl. No.: 10/416,631

(22) PCT Filed: Oct. 8, 2001

(86) PCT No.: PCT/FR01/03089

§ 371 (c)(1), (2), (4) Date: May 14, 2003

(87) PCT Pub. No.: WO02/45612

PCT Pub. Date: Jun. 13, 2002

(65) Prior Publication Data

US 2004/0033467 A1 Feb. 19, 2004

(30) Foreign Application Priority Data

Dec. 5, 2000 (FR) .................................. 00 15708

(51) Int. Cl.
*A61C 5/02* (2006.01)
(52) U.S. Cl. ....................................................... 433/102
(58) Field of Classification Search .................. 433/102, 433/81, 224, 141
See application file for complete search history.

(56) References Cited

U.S. PATENT DOCUMENTS

| 4,611,508 | A | 9/1986 | Roane |
| 4,850,867 | A | 7/1989 | Senia et al. |
| 5,380,200 | A | 1/1995 | Heath et al. |
| 5,588,835 | A | 12/1996 | Kert |
| 5,653,590 | A | 8/1997 | Heath et al. |
| 5,658,145 | A * | 8/1997 | Maillefer et al. ............. 433/102 |
| 5,676,541 | A | 10/1997 | Maillefer et al. |
| 5,855,479 | A | 1/1999 | Wong et al. |
| 5,857,852 | A * | 1/1999 | Garman ...................... 433/102 |
| 5,897,316 | A | 4/1999 | Buchanan |
| 6,206,695 | B1 | 3/2001 | Wong et al. |
| 6,293,794 | B1 * | 9/2001 | McSpadden ................. 433/102 |

FOREIGN PATENT DOCUMENTS

| DE | 19852931 | 3/2000 |
| EP | 0501255 | 9/1992 |
| EP | 0684019 | 11/1995 |
| EP | 0780100 | 6/1997 |
| WO | WO 9314714 | 8/1993 |

* cited by examiner

*Primary Examiner*—Melba Bumgarner
(74) *Attorney, Agent, or Firm*—Gary M. Cohen

(57) ABSTRACT

An instrument for reaming a root canal, in particular, in the apical zone, includes proximal portions for receiving a handle which allows the instrument to be used by hand or on the head of a dentist's contra-angle handpiece, and distal portions having a blade with a pointed tip of a known type. The active, cutting part of the blade has, from the pointed tip and continuing along the blade, two conical sections. In addition to the pointed tip, each of the conical sections has a greater conicity than the least distal part adjacent to it. The instrument is useful for reaming root canals using a sequence of instruments which avoid root weakening and the flow of filling material from the end of the canal.

1 Claim, 4 Drawing Sheets

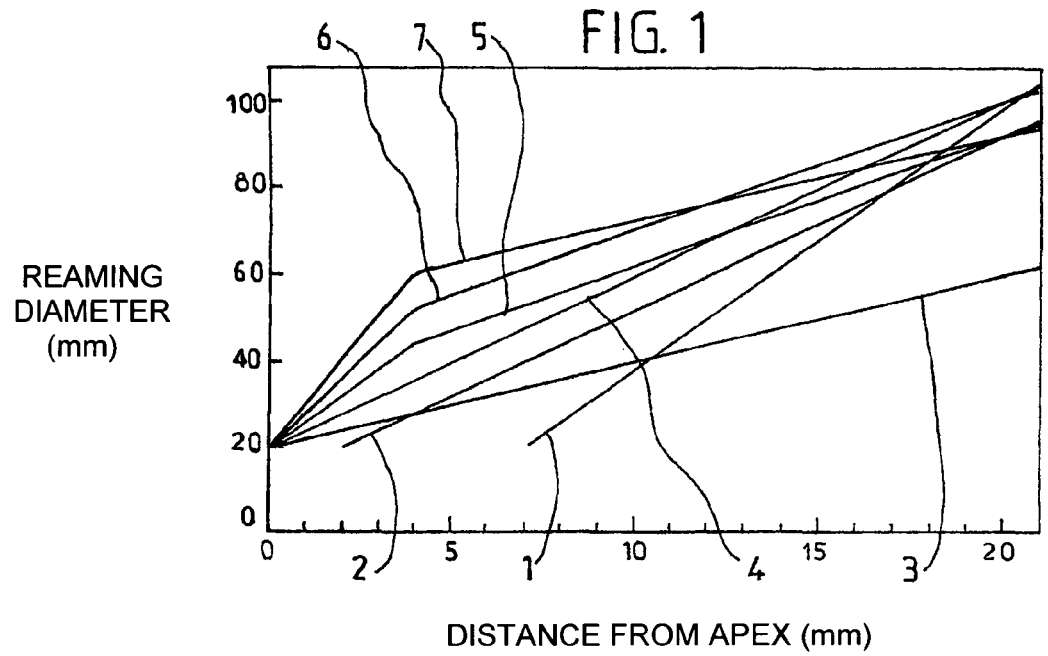
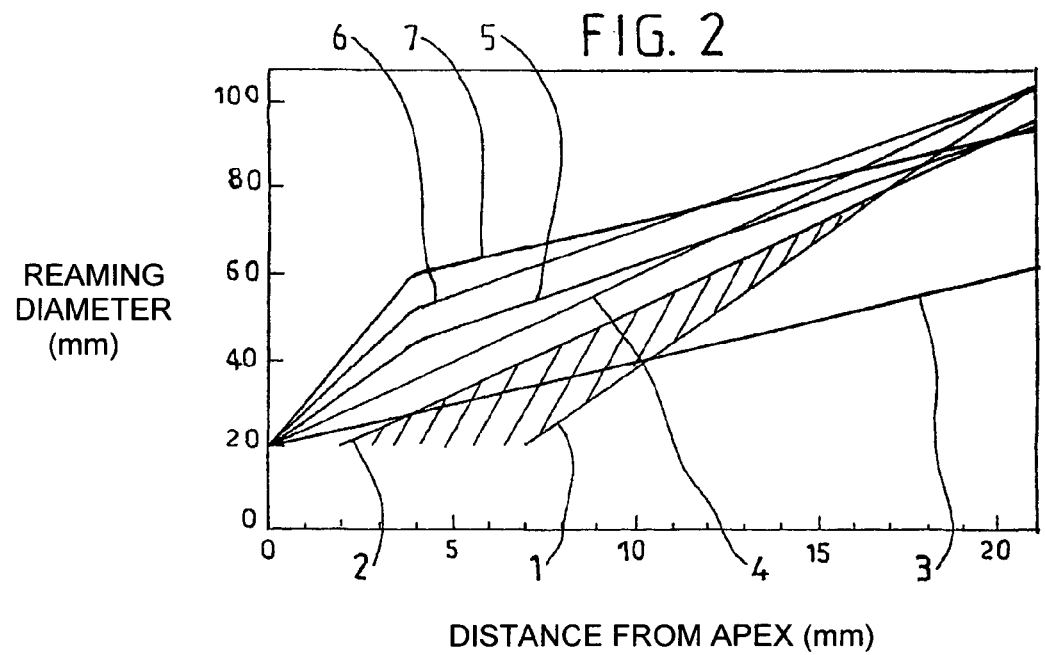

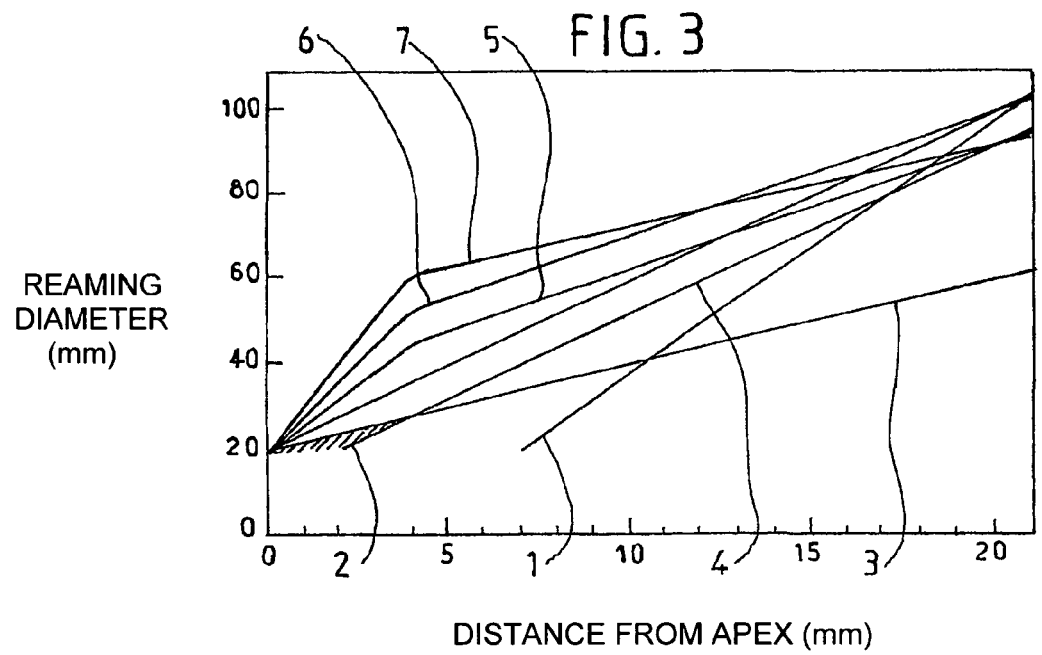
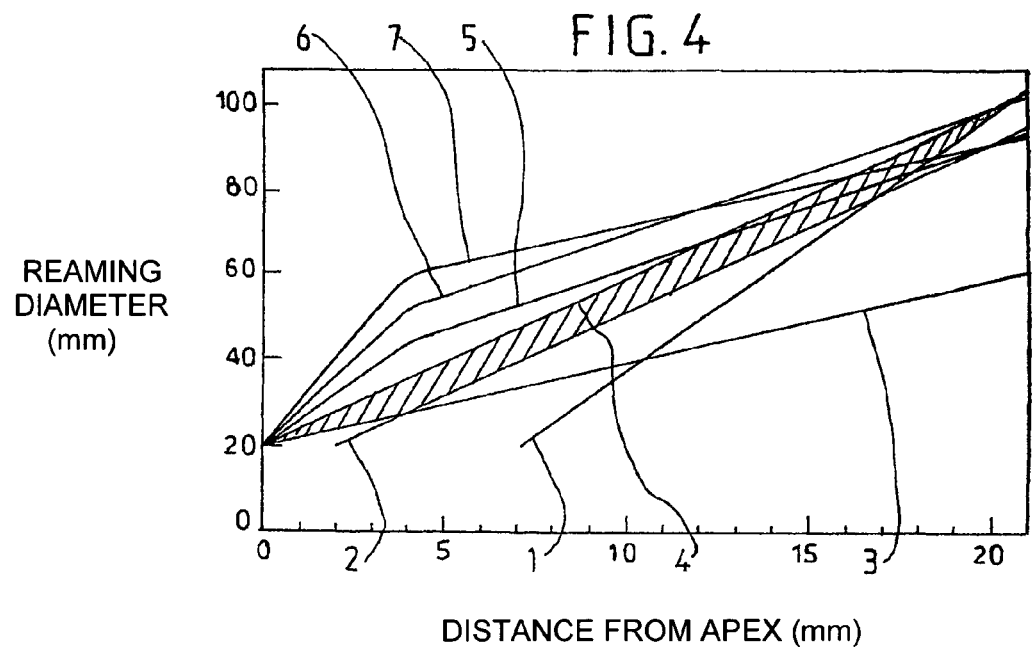

INSTRUMENT FOR REAMING ROOT CANALS AND SEQUENCE OF INSTRUMENTS COMPRISING AT LEAST SUCH AN INSTRUMENT

BACKGROUND OF THE INVENTION

The present invention relates to the field of endodontic instruments for the reaming of tooth canals, and more particularly, to a specific instrument for reaming tooth canals and a sequence of instruments comprising at least one such specific instrument.

Endodontic treatment involves a mechanical reaming of the root canal, followed by filling of the root canal, which is the final desired objective. Filling is done by adding an external material, for example, gutta-percha.

The gutta-percha is usually introduced into the prepared root canal in the form of a heated cone. Heating causes the gutta-percha to soften, rendering it malleable. The heated cones are condensed by mechanical action, with the aid of a rammer, in order to bring about "vertical" condensation or "lateral" condensation of the material relative to the longitudinal axis of the reamed root canal. The gutta-percha can also be arranged in the canal using the devices which are described in U.S. Pat. No. 5,588,835 or International Publication No. WO 93/14714.

Such techniques, and their purpose, are well known to the person skilled in the art and are widely used on a daily basis by practitioners.

In the operations performed for the mechanical preparation of a root canal, the practitioner generally attempts to preserve the anatomy of the root canal to the extent possible, in particular, to avoid weakening of the root as a result of an excessive removal of substance. The tendency is, therefore, toward minimum reaming of the canal. When this objective is observed, the result is a conical preparation having a small diameter at the apical level.

As a consequence of this, it is sometimes difficult to obtain a good filling with the methods described above. This is because such methods generally require, on the one hand, a wide canal preparation and, on the other hand, provision at the bottom of the canal of a seat-like bore which avoids the risk of the gutta-percha leaving the canal as a result of creep. It is, therefore, necessary to find a balance between these two constraints so as not to exaggerate the preparation in the upper part of the canal, which has the consequence of weakening the upper part of the canal.

SUMMARY OF THE INVENTION

The principal object of the present invention is to provide a specific instrument for the preparation of a root canal at the apical level which can solve the above-mentioned problems. Another object of the invention is to provide a sequence of endodontic instruments for the reaming of root canals which is comprised of at least one such specific instrument.

More precisely, the present invention relates to an instrument for reaming root canals, in particular, in the apical zone. Proximal portions of the instrument receive a handle which allows the instrument to be used by hand or on the head of a dentist's contra-angle handpiece. Distal portions of the instrument include a blade having a pointed tip of a type which is, per se, known. The blade has an active, cutting part which, starting from the pointed tip and continuing along the blade, has two conical sections. In addition to the pointed tip, each of the conical sections has a greater conicity than the least distal part immediately adjacent to it.

The present invention also relates to a sequence of endodontic instruments for the progressive reaming of root canals which comprise at least one instrument of the above type.

The invention will be better understood from the following description of an operating method which uses a sequence of instruments produced in accordance with the present invention, taken together with the following drawings.

BRIEF DESCRIPTION OF THE DRAWINGS

FIGS. 1 through 7 sequentially illustrate the progressive reaming of a root canal in order to obtain a desired root canal profile with an apical seat.

DETAILED DESCRIPTION OF THE INVENTION

For purposes of illustration, use of the following sequence of instruments is described. Instrument No. 1 has an apical diameter of 0.20 mm and a conicity of 6%. Instrument No. 2 has an apical diameter of 0.20 mm and a conicity of 4%. Instrument No. 3 has an apical diameter of 0.20 mm and a conicity of 2%. Instrument No. 4 is identical to Instrument No. 2. Instrument No. 5 has an apical diameter of 0.20 mm and a conicity of 6% along 4 mm of its active length, and then 3% along the remainder of the active length of the instrument. Instrument No. 6 has an apical diameter of 0.20 mm and a conicity of 8% along 4 mm of its active length, and then 3% along the remainder of the active length of the instrument. Instrument No. 7 has an apical diameter of 0.20 mm and a conicity of 10% along 4 mm of its active length, and then 2% along the remainder of the active length of the instrument.

The protocol begins with the use of Instrument No. 1, which gives the canal a profile (1) which is shown in FIG. 1. The instrument is engaged in the canal to a distance of approximately 7 mm from the apex. It will be seen that this first operation determines the maximum reaming diameter and, consequently, the minimum depth of the resulting canal.

The protocol continues with the use of Instrument No. 2, Instrument No. 3 and Instrument No. 4, which progressively ream the canal. Instrument No. 3 is the first instrument to be engaged to the apical level. It is this instrument which provides for the preparation of the apical diameter which will subsequently be observed by the remainder of the sequence.

Figure 5:
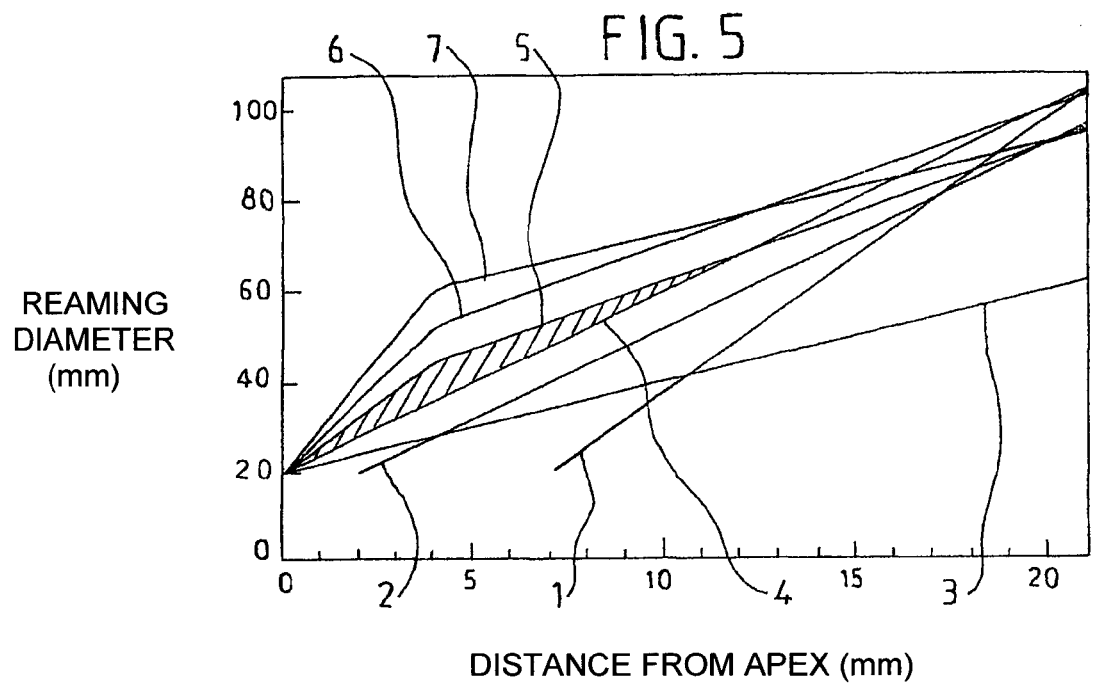
Figure 6:
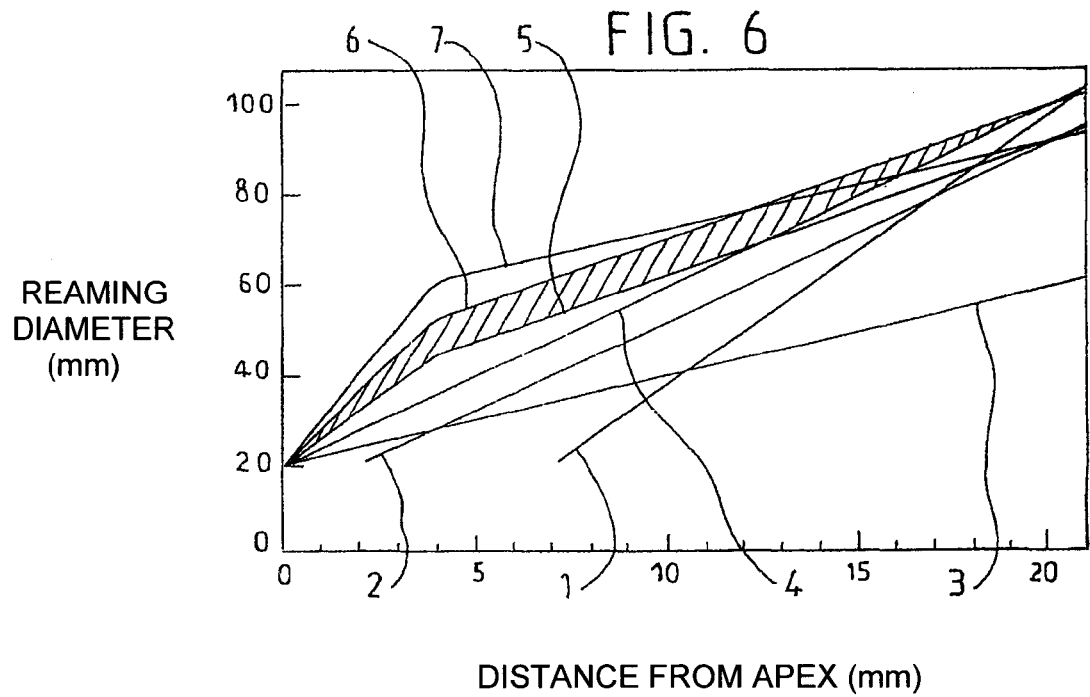
Figure 7:
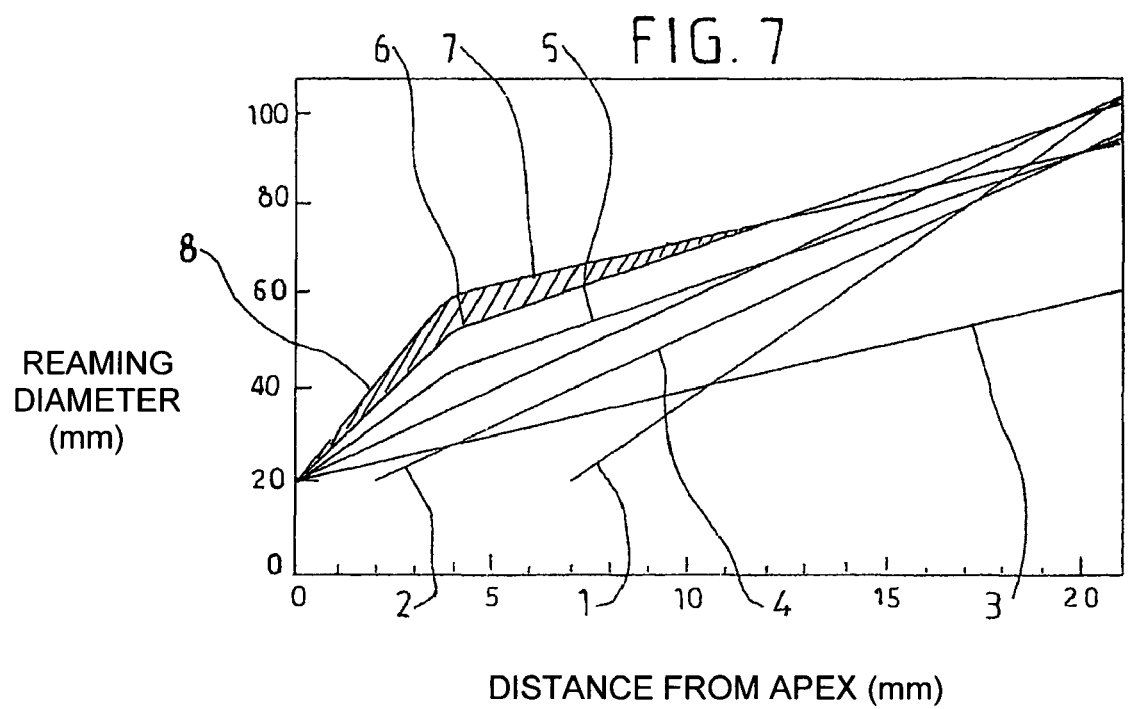

Instrument No. 5, Instrument No. 6 and Instrument No. 7 are then engaged, in sequence, each to the apical level. Substance is extracted progressively, as shown by the hatched areas in FIGS. 3, 4 and 5, in order to arrive at the desired profile of the canal, with an apical seat (8).

The above-described protocol has the following advantageous general characteristics. Within the same series of instruments, the conicity of the most distal part increases from one instrument to the next in their sequential order of use. Advantageously, at least two instruments in a series of the instruments have a conical part with the same conicity. This is, for instance, the case with Instrument No. 2 and Instrument No. 4 in the foregoing example. Advantageously, each conical section of each instrument has an identical conicity for all the instruments of the same sequence. As an alternative, for a given conical part, at least one instrument has a conicity different than that of the other instruments of the sequence, in their equivalent part.

The invention claimed is:

1. A sequence of instruments for preparing a root canal, particularly in an apical zone of the root canal, wherein the instruments include proximal portions for receiving a handle which allows the instruments to be used by hand or on a head of a contra-angle handpiece, and distal portions having a pointed tip, and wherein the sequence of instruments comprises at least one instrument having a blade with an active, cutting part having two conical sections which extend from the pointed tip and continuously along the blade, wherein, in combination with the pointed tip, each conical section of the instrument has a conicity which is greater than a conicity associated with a proximally oriented, immediately adjacent portion of the instrument, and wherein the sequence of instruments comprises seven instruments including:

- a first instrument having an apical diameter of 0.20 mm, wherein the first instrument includes a conical section having a conicity of 6%;
- a second instrument having an apical diameter of 0.20 mm, wherein the second instrument includes a conical section having a conicity of 4%;
- a third instrument having an apical diameter of 0.20 mm, wherein the third instrument includes a conical section having a conicity of 2%;
- a fourth instrument which is identical to the second instrument;
- a fifth instrument having an apical diameter of 0.20 mm, wherein the fifth instrument includes two conical sections having a first conicity of 6% for a distance of 4 mm along an active length of the fifth instrument, and a second conicity of 3% along remaining portions of the active length;
- a sixth instrument having an apical diameter of 0.20 mm, wherein the sixth instrument includes two conical sections having a first conicity of 8% for a distance of 4 mm along an active length of the sixth instrument, and a second conicity of 3% along remaining portions of the active length; and
- a seventh instrument having an apical diameter of 0.20 mm, wherein the seventh instrument includes two conical sections having a first conicity of 10% for a distance of 4 mm along an active length of the seventh instrument, and a second conicity of 2% along remaining portions of the active length.

* * * * *